(12) United States Patent
Pisak et al.

(10) Patent No.: US 9,283,220 B2
(45) Date of Patent: Mar. 15, 2016

(54) COMPOSITIONS OF OPIOID ANTAGONISTS AND METHODS FOR TREATING CONDITIONS CAUSED BY THE VARICELLA-ZOSTER VIRUS THEREWITH

(75) Inventors: Ibrahim Mustafa Iskender Pisak, Istanbul (TR); Semra Bingol, Istanbul (TR); Mehmet Levent Selamoglu, Istanbul (TR); Mehmet Pisak, Istanbul (TR)

(73) Assignee: IMUNEKS FARMA ILAC SANAYI VE TICARET ANONIM SIRKETI PAK IS MERKEZI, Istanbul (TR)

( * ) Notice: Subject to any disclaimer, the term of this patent is extended or adjusted under 35 U.S.C. 154(b) by 56 days.

(21) Appl. No.: 13/076,564

(22) Filed: Mar. 31, 2011

(65) Prior Publication Data

US 2011/0245278 A1    Oct. 6, 2011

(30) Foreign Application Priority Data

Mar. 31, 2010   (TR) .................................. 2010/02473

(51) Int. Cl.
| | |
|---|---|
| A61K 31/44 | (2006.01) |
| A61K 9/00 | (2006.01) |
| A61K 31/485 | (2006.01) |
| A61K 9/06 | (2006.01) |
| A61K 9/48 | (2006.01) |
| A61K 47/32 | (2006.01) |
| A61K 47/44 | (2006.01) |

(52) U.S. Cl.
CPC .............. *A61K 31/485* (2013.01); *A61K 9/0014* (2013.01); *A61K 9/06* (2013.01); *A61K 9/4866* (2013.01); *A61K 47/32* (2013.01); *A61K 47/44* (2013.01)

(58) Field of Classification Search
CPC   A61K 31/485; A61K 31/522; A61K 2300/00
USPC .......................................... 514/282; 424/400
See application file for complete search history.

(56) References Cited

U.S. PATENT DOCUMENTS

| | | | |
|---|---|---|---|
| 4,416,886 A |   | 11/1983 | Bernstein |
| 4,857,533 A |   | 8/1989 | Sherman et al. |
| 4,888,346 A |   | 12/1989 | Bihari et al. |
| 5,356,900 A | * | 10/1994 | Bihari et al. ................... 514/282 |
| 6,248,365 B1 |   | 6/2001 | Romisch et al. |
| 6,355,245 B1 |   | 3/2002 | Evans et al. |
| 6,384,044 B1 |   | 5/2002 | Bihari |
| 6,538,028 B1 |   | 3/2003 | Pierson, III et al. |
| 2003/0077301 A1 |   | 4/2003 | Mailbach et al. |
| 2003/0078246 A1 |   | 4/2003 | Sackeyfio et al. |
| 2003/0191147 A1 |   | 10/2003 | Sherman et al. |
| 2003/0235542 A1 |   | 12/2003 | Mailbach et al. |
| 2003/0235627 A1 |   | 12/2003 | Mailbach et al. |
| 2005/0038062 A1 | * | 2/2005 | Burns et al. .................... 514/282 |
| 2006/0002874 A1 |   | 1/2006 | Mailbach et al. |
| 2006/0069086 A1 |   | 3/2006 | Michalow |
| 2007/0299098 A1 | * | 12/2007 | Tanabe .......................... 514/282 |
| 2011/0082167 A1 |   | 4/2011 | Pisak et al. |
| 2011/0165232 A1 |   | 7/2011 | Pisak et al. |

FOREIGN PATENT DOCUMENTS

| | | | |
|---|---|---|---|
| WO | WO 00/01390 | * | 1/2000 |
| WO | WO 2010/032073 |   | 3/2010 |

OTHER PUBLICATIONS

Johnson et al. "Management of herpes zoster (shingles) and postherpetic neuralgia," Expert Opin. Pharmacother. 2004, vol. 5, No. 3, pp. 551-559.*
The Merck Manual, Fifteenth Edition, 1987, Merck & Co. Inc. p. 168-169.*
I.S. Zagon & P.J. McLaughlin, "Naltrexone modulates tumor response in mice with neuroblastoma", Science, 221: 671-3 (Aug. 12, 1983).
E.A. Moore & S. Wilkinson, The Promise of Low Dose Naltrexone Therapy: Potential Benefits in Cancer, Autoimmune, Neurological and Infectious Disorders (McFarland & Company, Inc., Publishers, 2009)—Table of Contents.
Herpes zoster opthalmicus, The Merck manual of diagnosis and therapy, The Merck manuals online medical library. http://www.merck.com/mmpe/sec09/ch102/ch102e.html#sec09-ch102-ch102e-355, Oct. 2008.
Silman A. J., "Mortality from scleroderma in England and Wales 1968-1975," *Ann. Rheu. Dis.* 50: 95-96 (1991).
Smith, Textbook of the Autoimmune Diseases, Edited by Lahita, Chiorazzi and Reeves, Lippincott Williams & Wilkins, Philadelphia 2000—Table of Contents.
Clements P. J. and Furst D. E. (1996) "Systemic Sclerosis" Williams and Williams, Baltimore—Table of Contents.
Strehlow D. and Korn J, "Biology of the scleroderma fibroblast." *Curr. Opin. Rheumatol.* 10: 572-578 (1998).
LeRoy E. C., "Increased collagen synthesis by scleroderma skin fibroblasts in vitro," *J. Clin. Invest.* 54: 880-889 (1974).
Martini, Maccado, Ravelli et al., *Arthritis Rheum.* 42: 807-811 (1999).
"Risk factors associated with age-related macular degeneration—A case-control study in the age-related eye disease study: Report No. 3," *Ophthalmology*, 107 (12): 2224-2232 (2000).
Van der Schaft TL, de Bruijn WC, Mooy CM, Ketelaars DA, de Jong PT, "Element analysis of the early stages of age- related macular degeneration," *Arch. Ophthalmol.*, 110(3): 389-94 (1992).
Lengyel I, Flinn JM, Peto T, et al. "High concentration of zinc in sub-retinal pigment epithelial deposits," *Exp. Eye Res.*, 84(4): 772-80 (2007).
Hageman GS, Luthert PJ, Victor Chong NH, Johnson LV, Anderson DH, Mullins RF, "An integrated hypothesis that considers drusen as biomarkers of immune-mediated processes at the RPE-Bruch's membrane interface in aging and age-related macular degeneration," *Prog Retin Eye Res.*, 20 (6): 705-732 (2001).

(Continued)

*Primary Examiner* — Shengjun Wang
(74) *Attorney, Agent, or Firm* — Wilson Sonsini Goodrich & Rosati

(57) ABSTRACT

Provided are compositions comprising opioid antagonists, such as naltrexone naloxone, or nalmefene, or their pharmaceutically acceptable salts, and methods for treating conditions caused by the varicella-zoster virus therewith.

29 Claims, No Drawings

(56) References Cited

OTHER PUBLICATIONS

Patel N, Adewoyin T, Chong NV, "Age-related macular degeneration: a perspective on genetic studies", *Eye*, 22(6):768-776 (2008).

Zagon IS, Rahn KA, McLaughlin PJ, (2007) "Opioids and migration, chemotaxis, invasion, and adhesion of human cancer cells". *Neuropeptides*, 41 (6) : 441-452.

J.C. Ballantyne, J. Mao, "Opioid Therapy for Chronic Pain," *N. Eng. J. Med.* 349: 1943-1953 (Nov. 13, 2003).

U.S. Appl. No. 12/892,046, filed Sep. 28, 2010, entitled *Topical Compositions of Opioid Antagonists and Methods for Treating Skin Conditions Therewith*.

U.S. Appl. No. 13/076,590, filed Mar. 31, 2011, entitled *Compositions of Opioid Antagonists and Methods for Treating Scleroderma Therewith*.

Non-final office action mailed on Dec. 13, 2011 in connection with co-pending U.S. Appl. No. 12/892,046, currently under examination.

Herpes zoster opthalmicus, The Merck manual of diagnosis and theraphy. The Merck manuals online medical library. http://www.merck.com/mmpe/sec09/ch102/ch102e.html//sec09-ch102-ch102e-355, Accessed Jan. 6, 2010.

Office action dated Jan. 25, 2012 for U.S. Appl. No. 12/892,046.

The eye digest, ( 2007) Eye & Ear Infirmary, University of Illinois, http://www.agingeye.net/maculardegen/maculardegennewdevelopments.php, Accessed May 24, 2012.

Office action dated Nov. 7, 2012 for U.S. Appl. No. 13/119,191.

San-Emeterio, et al. Modulation of brain apoptosis-related proteins by the opioid antagonist naltrexone in mice. Neurosci Lett. Aug. 7, 2006;403(3):276-9. Epub May 22, 2006.

Webster, L. R. Oxytrex: an oxycodone and ultra-low-dose naltrexone formulation. Expert Opin Investig Drugs. Aug. 2007;16(8):1277-83.

Clements P. J. and Furst D. E. (1996) "Systemic Sclerosis" Williams and Williams, Baltimore.

E.A. Moore & S. Wilkinson, The Promise of Low Dose Naltrexone Therapy: Potential Benefits in Cancer, Autoimmune, Neurological and Infectious Disorders (McFarland & Company, Inc., Publishers, 2009).

Ni, et al. Neuroprotective Effects of Naloxone against Light-Induced Photoreceptor Degeneration through Inhibiting Retinal Microglial Activation. Invest. Ophthalmol. Vis. Sci. Jun. 2008 vol. 49 No. 6 2589-2598.

Office action dated Aug. 28, 2013 for U.S. Appl. No. 13/119,191.

Office action dated Oct. 16, 2013 for U.S. Appl. No. 13/076,590.

Smith, Textbook of the Autoimmune Diseases, Edited by Lahita, Chiorazzi and Reeves, Lippincott Williams & Wilkins, Philadelphia 2000.

Blaylock. Chronic microglial activation and excitotoxicity secondary to excessive immune stimulation: possible factors in Gulf War Syndrome and autism. Journal of American Physicians and Surgeons. 2004; 9(2):46-51.

Jiang, et al. Inhibition of LPS-induced retinal microglia activation by naloxone does not prevent photoreceptor death. Inflammation. Feb. 2013;36(1):42-52. doi: 10.1007/s10753-012-9518-6. (abstract only).

Ni, et al. Neuroprotective effects of naloxone against light-induced photoreceptor degeneration through inhibiting retinal microglial activation. Invest Ophthalmol Vis Sci. Jun. 2008;49(6):2589-98. doi: 10.1167/iovs.07-1173.

Office action dated Feb. 10, 2015 for U.S. Appl. No. 13/119,191.

Office action dated Apr. 28, 2014 for U.S. Appl. No. 13/076,590.

Office action dated Jul. 1, 2014 for U.S. Appl. No. 13/119,191.

Office action dated Oct. 10, 2014 for U.S. Appl. No. 13/076,590.

Shen, et al. Naloxone ameliorates retinal lesions in Cc12/Cx3crl double-deficient mice via modulation of microglia. Invest Ophthalmol Vis Sci. May 2, 2011;52(6):2897-904. doi: 10.1167/iovs.10-6114.

Smith. Scleroderma, Textbook of the Autoimmune Diseases, 2000, chapter 28, edited by Lahita, R.G., pp. 557-567.

Office action dated Aug. 5, 2015 for U.S. Appl. No. 13/076,590.

Office action dated Aug. 13, 2015 for U.S. Appl. No. 13/119,191.

* cited by examiner

COMPOSITIONS OF OPIOID ANTAGONISTS AND METHODS FOR TREATING CONDITIONS CAUSED BY THE VARICELLA-ZOSTER VIRUS THEREWITH

CROSS-REFERENCE TO RELATED APPLICATIONS

This application claims the benefit of priority to Turkish patent application No. TR 2010/02473, filed on Mar. 31, 2010, the contents of which are herein incorporated by reference in their entirety.

FIELD OF THE INVENTION

The invention relates to compositions comprising opioid antagonists, such as naltrexone, naloxone, or nalmefene, or their pharmaceutically acceptable salts, and methods for treating conditions caused by the varicella-zoster virus, such as herpes zoster disease, therewith.

BACKGROUND OF THE INVENTION

Naltrexone has the chemical name morphinan-6-one, 17-(cyclopropylmethyl)-4,5-epoxy-3,14-dihydroxy-(5α). The molecular formula of naltrexone is $C_{20}H_{23}NO_4$ and its molecular weight is 341.41 in the anhydrous form (<1% maximum water content). The chemical structure of naltrexone is shown below.

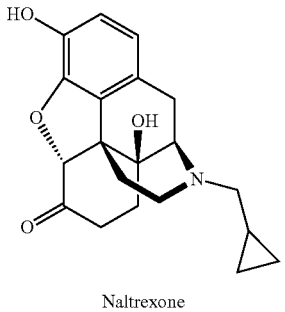

Naltrexone

Naltrexone has been approved for use in the treatment of alcoholism or narcotic addiction. It is believed that naltrexone functions by blocking the brain receptors that trigger the effects of alcohol or narcotics. Naltrexone is marketed by Durmed in the form of a tablet under the tradename ReVia® and by Alkermes in the form of a powder for injectable suspension under the tradename Vivitrol®.

Naloxone has the chemical name (−)-17-allyl-4,5α-epoxy-3,14-dihydroxymorphinan-6-one and the molecular formula $C_{19}H_{21}NO_4$. The chemical structure of naloxone is shown below.

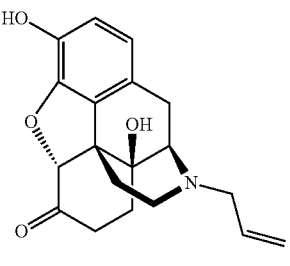

Naloxone

Naloxone is typically administered intravenously because of its short duration of action, and is generally administered to a patient in order to reverse opioid depression, including respiratory depression, induced by natural and synthetic opioids.

Nalmefene has the chemical name 17-cyclopropylmethyl-4,5α-epoxy-6-methylenemorphinan-3,14-diol and the molecular formula $C_{21}H_{25}NO_3$. The chemical structure of nalmefene is shown below.

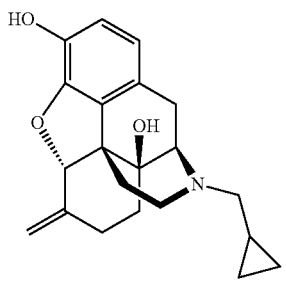

Nalmefene

Nalmefene is typically used in the management of alcohol dependence, and also has been investigated for the treatment of other addictions such as pathological gambling and addiction to shopping. Advantages of nalmefene relative to naltrexone include longer half-life, greater oral bioavailability and no observed dose-dependent liver toxicity. As with other drugs of this type, nalmefene can precipitate acute withdrawal symptoms in patients who are dependent on opioid drugs, or more rarely when used post-operatively to counteract the effects of strong opioids used in surgery.

In the early 1980s, it was reported that the administration of low dose naltrexone (less than 10 mg naltrexone per day) increases the production of endogenous endomorphins, especially the endogenous pentapeptide metenkephalin, and increases the number and density of metenkephalin receptors by intermittently blocking opiate receptors. (I. S. Zagon & P. J. McLaughlin, "Naltrexone modulates tumor response in mice with neuroblastoma", *Science,* 221: 671-3 (12 Aug. 1983). This increase in metenkephalin is believed to enhance homeostatic regulation of the natural immune function of the human body.

In view of Zagon's findings, Bernard Bihari reported the use of low dose naltrexone for the treatment of patients with AIDS (U.S. Pat. No. 4,888,346) and herpes (U.S. Pat. No. 5,356,900). Further, Nicholas Plotnikoff reported the use of low dose naltrexone for the treatment of herpes, HIV infection, cytomegalovirus, coronavirus, influenza A and Japanese encephalitis. (E. A. Moore & S. Wilkinson, THE PROMISE OF LOW DOSE NALTREXONE THERAPY: POTENTIAL BENEFITS IN CANCER, AUTOIMMUNE, NEUROLOGICAL AND INFECTIOUS DISORDERS (McFarland & Company, Inc., Publishers, 2009)).

Herpes zoster (or shingles) is a disease caused by the reactivation of the varicella-zoster virus (VZV). The VZV causes chickenpox (or varicella) generally during childhood and can lie in a dormant state in nerve cells along the spine afterwards. The VZV can re-emerge later as shingle, most commonly in adults, especially those over the age of 60 or those with weak immune systems. One of the major symptoms of shingles is a unilateral vesicular eruption with dermatomal distribution. The onset of the disease is often preceded by pain 48 to 72 hours before the rash develops in the affected dermatome. The rash may appear as erythematous, maculopapular lesions that rapidly evolve into vesicles. The vesicles may coalesce and form bullous lesions. The lesions may continue to form for 3 to 5 days, with a total duration of the disease of 10 to 15 days. However it can take as long as 1 month before the skin returns to normal.

Herpes zoster can also affect the surrounding regions of the eye and the eye itself. This is called herpes zoster ophthalmicus—the reactivation of a varicella-zoster virus infection involving the eye. Symptoms and signs, which may be intense, include dermatomal forehead rash and painful inflammation of all the tissues of the anterior and, rarely, posterior structures of the eye. Complications may include: keratitis accompanied by uveitis; late sequelae, such as glaucoma, cataract, chronic or recurrent uveitis, corneal scarring, corneal neovascularization, or hypesthesia; and postherpetic neuralgia. (Herpes zoster opthalmicus, The Merck manual of diagnosis and therapy, The Merck manuals online medical library. http://www.merck.com/mmpe/sec09/ch102/ch102e.html#sec09-ch102-ch102e-355, Accessed Jan. 6, 2010). Current treatments for herpes zoster include topical, oral, or ophthalmic administration of an antiviral agent, such as acyclovir, valacyclovir or famciclovir.

SUMMARY OF THE INVENTION

In one embodiment, the invention encompasses methods for treating a condition caused by the varicella-zoster virus comprising administering to a subject in need thereof an effective amount of an opioid antagonist or a pharmaceutically acceptable salt thereof.

In another embodiment, the invention encompasses kits comprising a unit dose of an opioid antagonist and a label or printed instructions instructing the administration of the opioid antagonist to treat a condition caused by the varicella-zoster virus.

DETAILED DESCRIPTION OF THE INVENTION

The present invention provides methods for treating conditions caused by the varicella-zoster virus comprising administering to a subject in need thereof an effective amount of an opioid antagonist or a pharmaceutically acceptable salt thereof. In one embodiment, the opioid antagonist or pharmaceutically acceptable salt thereof is topically administered to the subject.

As used herein, an "effective amount" is an amount effective for treating a condition caused by the varicella-zoster virus.

As used herein, the term "treating" a condition caused by the varicella-zoster virus in a subject refers to subjecting the subject to a pharmaceutical treatment, e.g., the administration of one or more agents, such that at least one symptom of the condition is decreased or prevented from worsening.

Conditions caused by the varicella-zoster virus include, but are not limited to herpes zoster disease (also called shingles). Conditions associated with herpes zoster disease include, but are not limited to shingles vesicular rash, postherpetic neuralgia, zoster multiplex, zoster sine herpete, myelitis, Ramsay-Hunt syndrome, and herpes zoster ophthalmicus.

In one embodiment, the condition caused by the varicella-zoster virus is herpes zoster disease. Herpes zoster disease may include shingles vesicular rash, postherpetic neuralgia, zoster multiplex, zoster sine herpete, myelitis, Ramsay-Hunt syndrome, and herpes zoster ophthalmicus.

Suitable opioid antagonists include compounds that block one or more opioid receptors. In some embodiments, the opioid antagonist selectively blocks the mu (μ) opioid receptor, the delta (δ) opioid receptor, or the kappa (κ) opioid receptor. In other embodiments, the opioid antagonist is non-selective. Examples of opioid antagonists include, but are not limited to, naltrexone, naloxone, nalorphine, levallorphan, nalmefene, cyprodime, naltindole, and norbinaltorphimine. In one embodiment, the opioid antagonist is naltrexone. In another embodiment, the opioid antagonist is naloxone. In another embodiment, the opiod antagonist is nalmefene.

In some embodiments, the opioid antagonist is a compound that may exist in the form of one or more stereoisomers, wherein one or more of those stereoisomers is therapeutically active. In some embodiments, the opioid antagonist comprises a therapeutically active stereoisomer that is substantially free of other stereoisomers. In other embodiments, the opioid antagonist comprises a therapeutically active stereoisomer that has less than about 50%, less than about 40%, less than about 30%, less than about 20%, less than about 10%, less than about 5%, or less than about 1% by weight of other stereoisomers.

The opioid antagonist is typically administered to the subject in the form of a composition for topical, oral, or ophthalmic administration. In some embodiments, the composition comprises an effective amount of the opioid antagonist and at least one pharmaceutically acceptable excipient.

Compositions for Topical Administration

In some embodiments, the opioid antagonist is administered to the subject in the form of a composition for topical administration.

In some embodiments, the opioid antagonist is present in an amount of about 0.1% to about 5% by weight of the composition. In other embodiments, the opioid antagonist is present in an amount of about 0.5% to about 4%, about 0.5% to about 2%, about 0.5% to about 1.5%, about 1% to about 4%, about 1% to about 3%, about 1% to about 2%, about 2% to about 3%, about 2% to about 4%, about 3% to about 4%, or about 1% by weight of the composition.

The pharmaceutically acceptable excipient may be any topically acceptable non-transdermally effective excipient known by those skilled in the art. Suitable excipients include, but are not limited to, emulsifying agents, stiffening agents, rheology modifiers or thickeners, surfactants, emollients, preservatives, humectants, alkalizing or buffering agents, and solvents.

Suitable emulsifying agents include, but are not limited to cetyl alcohol, cetostearyl alcohol, stearyl alcohol, carboxypolymethylene, polycarbophil, polyethylene glycol, and sorbitan esters. Suitable stiffening agents include, but are not limited to stearyl alcohol, cetostearyl alcohol, and cetyl alcohol. Suitable rheology modifiers or thickeners include, but are not limited to, carbomers such as Carbopol®, and polyoxyethylene tallow amines such as Ethomeen®. Suitable surfactants include, but are not limited to, anionic, cationic, amphoteric, and nonionic surfactants. In some embodiments, the surfactant is sodium lauryl sulfate, cetostearyl alcohol, cetyl alcohol, magnesium lauryl sulfate, a wax, or a combination thereof. Suitable emollients include, but are not limited to, white petrolatum (while vaseline), liquid petrolatum (liquid vaseline), paraffin, or aquaphor. Suitable preservatives include, but are not limited to, antimicrobial preservatives such as nipagin (methyl hydroxybenzoate), nipasol (hydroxybenzoate), butylparaben, ethylparaben, methylparaben, propyl paraben potassium, and propyl paraben sodium. Suitable humectants include, but are not limited to, propylene glycol and propylene glycol alginate. Suitable alkalizing or buffering agents include, but are not limited to, sodium hydroxide and potassium hydroxide. Suitable solvents include, but are not limited to, water.

The composition may be in the form of a gel, cream, ointment, liquid, suspension, solution, emulsion, foam, aerosol or the like for topical administration. Typically, the composition is administered to the subject by spreading (e.g., gel, cream, or ointment) or spraying (e.g., liquid or aerosol) onto the affected area of the skin.

In one embodiment, the composition is in the form of a cream. Typically, the cream comprises an opioid antagonist and one or more of an emulsifying agent, a stiffening agent, a surfactant, an emollient, a preservative, a humectant, an alkalizing or buffering agent, and a solvent. In some embodiments, the cream has a formulation according to Table 1a, 1b, or 1c.

TABLE 1a

Illustrative Cream Formulation

| Ingredient | Amount (% by weight of the composition) |
|---|---|
| Opioid antagonist | about 0.1%-5% |
| Emulsifying agent | about 2%-5% |
| Stiffening agent | about 1%-45% |
| Surfactant | about 0.5%-2.5% |
| Preservative | about 0.01%-0.6% |
| Humectant | about 1%-15% |
| Alkalizing or buffering agent | about 0.01%-3% |
| Emollient | about 1%-50% |
| Solvent | q.s |

TABLE 1b

Illustrative Cream Formulation

| Ingredient | Amount (% by weight of the composition) |
|---|---|
| Opioid antagonist | about 0.5%-2% |
| Emulsifying agent | about 2%-5% |
| Stiffening agent | about 2%-5% |
| Surfactant | about 0.5%-1.5% |
| Preservative | about 0.01%-0.6% |
| Humectant | about 2%-10% |
| Alkalizing or buffering agent | about 0.01%-3% |
| Emollient | about 15%-30% |
| Solvent | q.s |

TABLE 1c

Illustrative Cream Formulation

| Ingredient | Amount (% by weight of the composition) |
|---|---|
| Opioid antagonist | about 0.5%-2% |
| Cetyl alcohol and/or carboxypolymethylene | about 2%-5% |
| Stearyl alcohol | about 2%-5% |
| Sodium lauryl sulfate | about 0.5%-1.5% |
| Nipagin and/or Nipasol | about 0.01%-0.6% |
| Propylene glycol | about 2%-10% |
| Sodium hydroxide | about 0.01%-3% |
| White vaseline and/or liquid vaseline | about 15%-30% |
| Water | q.s. |

In one embodiment, the composition is in the form of an ointment. Typically, the ointment comprises an opioid antagonist and one or more of an emulsifying agent, an emollient, and a preservative. In some embodiments, the ointment has a formulation according to Table 2a, 2b, or 2c.

TABLE 2a

Illustrative Ointment Formulation

| Ingredient | Amount (% by weight of the composition) |
|---|---|
| Opioid antagonist | about 0.1%-5% |
| Emulsifying agent | about 1%-10% |
| Preservative | about 0.01%-0.6% |
| Emollient | q.s |

TABLE 2b

Illustrative Ointment Formulation

| Ingredient | Amount (% by weight of the composition) |
|---|---|
| Opioid antagonist | about 0.5%-2% |
| Emulsifying agent | about 2%-5% |
| Preservative | about 0.01%-0.6% |
| Emollient | q.s. |

TABLE 2c

Illustrative Ointment Formulation

| Ingredient | Amount (% by weight of the composition) |
|---|---|
| Opioid antagonist | about 0.5%-2% |
| Polyoxyethylene 20 sorbitan monooleate | about 2%-5% |
| Nipagin and/or Nipasol | about 0.01%-0.6% |
| White vaseline and/or liquid vaseline | q.s. |

In one embodiment, the composition is in the form of a gel. Typically, the gel comprises an opioid antagonist and one or more of a rheology modifier or thickener, an alkalizing or buffering agent, and a solvent. In some embodiments, the gel has a formulation according to Table 3a, 3b, or 3c.

TABLE 3a

Illustrative Gel Formulation

| Ingredient | Amount (% by weight of the composition) |
|---|---|
| Opioid antagonist | about 0.1%-5% |
| Rheology modifier or thickener | about 0.5%-2% |
| Alkalizing or buffering agent | about 0.5%-10% |
| Solvent | q.s. |

TABLE 3b

Illustrative Gel Formulation

| Ingredient | Amount (% by weight of the composition) |
|---|---|
| Opioid antagonist | about 0.5%-2% |
| Rheology modifier or thickener | about 1%-2% |
| Alkalizing or buffering agent | about 0.5%-5% |
| Solvent | q.s |

TABLE 3c

Illustrative Gel Formulation

| Ingredient | Amount (% by weight of the composition) |
|---|---|
| Opioid antagonist | about 0.5%-2% |
| Carbomer | about 1%-2% |
| Sodium hydroxide | about 0.5%-5% |
| Water | q.s |

Typically, the opioid antagonist is administered to the subject in a total daily dose of up to about 150 mg/cm$^2$ of skin. In some embodiments, the opioid antagonist is administered to the subject in a total daily dose of about 5 mg/cm$^2$ of skin to about 150 mg/cm$^2$ of skin, about 10 mg/cm$^2$ of skin to about 100 mg/cm$^2$ of skin, about 20 mg/cm$^2$ of skin to about 90 mg/cm$^2$ of skin, about 30 mg/cm$^2$ of skin to about 80 mg/cm$^2$ of skin, about 40 mg/cm$^2$ of skin to about 70 mg/cm$^2$ of skin, or about 50 mg/cm$^2$ of skin or about 60 mg/cm$^2$ of skin. The total daily dose may be delivered once per day, or divided between multiple doses. In some embodiments, the opioid antagonist is administered 1, 2, 3, 4, or 5 times per day.

Compositions for Oral Administration

In some embodiments, the opioid antagonist is administered to the subject in the form of a composition for oral administration. The oral composition may be in the form of a tablet, capsule, caplet, granule, powder, lozenge, troche, dragee, sachet, cachet, liquid, solution, suspension, emulsion, elixir, or syrup for oral administration. In one embodiment, the oral composition is in the form of a tablet or capsule. The tablet may be in the form of an uncoated tablet, coated tablet (for example with sugar or an enteric coating), effervescent tablet, dispersible tablet, orally-dissolving tablet, or sublingual tablet.

In one embodiment, the oral composition comprises an effective amount of an opioid antagonist and at least one pharmaceutically acceptable excipient. Suitable pharmaceutically acceptable excipients for the above solid oral compositions include, but are not limited to, starches, sugars, diluents, granulating agents, lubricants, binders, disintegrating agents and the like. Suitable pharmaceutically acceptable excipients for the above liquid oral compositions include, but are not limited to, water, glycols, oils, alcohols, flavoring agents, preservatives, coloring agents and the like.

Typically, the opioid antagonist is present in the oral composition in an amount of about 0.1 mg to about 10 mg, about 0.5 mg to about 8 mg, about 1 mg to about 6 mg, or about 1 mg to about 4.5 mg. In one embodiment, the opioid antagonist is present in the oral composition in an amount of about 2 mg.

Compositions for Ophthalmic Administration

In some embodiments, the opioid antagonist is administered to the subject in the form of a composition for ophthalmic administration. The ophthalmic composition may be in the form of a solution or a suspension.

In one embodiment, the ophthalmic composition comprises an effective amount of an opioid antagonist and at least one pharmaceutically acceptable excipient. Suitable pharmaceutically acceptable excipients for the ophthalmic compositions include those known by the skilled artisan to be suitable for ophthalmic administration.

Typically, the opioid antagonist is present in the ophthalmic composition in an amount of about 0.1% to about 10% by weight of the composition.

The topical, oral, and ophthalmic compositions described above may be administered to the subject daily, every other day, three times a week, twice a week, once a week, or at other appropriate intervals. In some embodiments, the composition is administered until there is complete healing of the condition caused by the varicella-zoster virus in the affected area.

The present invention may use lower doses of opioid antagonist than the doses conventionally used for oral administration in the treatment of alcohol or narcotic addiction. The opioid antagonist is administered to the individual in an amount effective to treat the condition caused by the varicella-zoster virus. In certain embodiments, the exact dose of opioid antagonist depends upon, by way of non-limiting example, the form in which the opioid antagonist is administered, the subject to be treated, the age, body weight and/or height of the subject to be treated, the preference and experience of the attending physician, the specific opioid antagonist used, the characteristics of the patient, and/or the nature of the condition for which the treatment is sought. Thus, in some embodiments, the dosage of opioid antagonist administered may vary from those disclosed herein. In various embodiments, these factors are determined by those of skill in the medical and pharmaceutical arts in view of the present disclosure.

The methods of the invention may further comprise administration of one or more additional agents effective to treat the condition caused by the varicella-zoster virus. Where the condition is herpes zoster disease, the additional agent may include, but not be limited to an antiviral agent such as acyclovir, valacyclovir or famciclovir. The additional agent and the opioid antagonist may be administered concurrently or separately. When administered concurrently, the additional agent and the opioid antagonist may be administered in the same or separate compositions.

In another embodiment, the invention encompasses kits comprising a unit dose of opioid antagonist. In one embodiment the unit dose is within a container, which can be sterile, containing an effective amount of opioid antagonist and a pharmaceutically acceptable excipient. The kits can further comprise a label or printed instructions instructing the use of the opioid antagonist to treat a condition caused by the varicella-zoster virus. The kits can further comprise a device that is useful for administering the unit dose as described herein. Examples of such a device include, but are not limited to, a wand, a dropper, a cotton swab, a pad, or the like.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1

Treatment of Vesicular Eruption with a Topical Composition of Naltrexone 100 g of naltrexone 1% cream was prepared by mixing 1 g of naltrexone hydrochloride in 99 g of a cream base containing the following excipients: cetyl alcohol, stearyl alcohol, sodium lauryl sulfate, vaseline, nipagin, nipasol, carboxypolymethylene, propyleneglycol, sodium hydroxide and distilled water.

A 26 year old man with vesicular eruption of herpes zoster on his right forearm and symptoms including hyperesthesia (oversensitivity), itching and pain, was treated with the 1% naltrexone cream described above. The naltrexone cream was administered to the affected area three times daily (morning, noon, and evening) in a total daily amount of 1 g, and the itching, pain and hyperesthesia disappeared after 3 days of treatment. In addition, the vesicular eruption regressed and completely disappeared after 5 days of treatment. No side effects were observed and additional treatment was unnecessary.

Example 2

Treatment of Vesicular Eruption with an Oral Composition of Naltrexone

Naltrexone capsules having the following formulation were prepared.

TABLE 4

Naltrexone Capsule

| Ingredient | Content |
| --- | --- |
| Naltrexone hydrochloride | 2.00 mg |
| Magnesium stearate | 0.18 mg |
| Microcristalline cellulose | q.s. 90.00 mg |
| Gelatin capsule No 4 | 1 |

A 53 year old man with a vesicular eruption (rash) in the form of a belt located on his upper back and symptoms including itching and pain, was treated with the naltrexone capsules described above. One naltrexone capsule as described above was administered once daily before bedtime in an amount of 2 mg, and the itching and pain disappeared after 4 days of treatment. The rash completely disappeared after 5 days of treatment. No side effects were observed and additional treatment was unnecessary.

Example 3

Naltrexone Topical Formulations

The following are illustrative naltrexone formulations according to the present invention.

TABLE 5

Illustrative Naltrexone Cream Formulation

| Ingredient | Amount (% by weight of the composition) |
| --- | --- |
| Naltrexone | 1% |
| Cetyl alcohol | 3.6% |
| Stearyl alcohol | 3.6% |
| Sodium lauryl sulfate | 0.8% |
| Nipagin | 0.1% |
| Nipasol | 0.05% |
| Carboxylpolymethylene | 0.2% |
| Propylene glycol | 5% |
| Sodium hydroxide | 0.03% |
| White vaseline | 13.5% |
| Liquid vaseline | 5.4% |
| Water | q.s |

TABLE 6

Illustrative Naltrexone Ointment Formulation

| Ingredient | Amount (% by weight of the composition) |
| --- | --- |
| Naltrexone | 1% |
| Polyoxyethylene 20 sorbitan monooleate | 4% |
| Nipagin | 0.18% |
| Nipasol | 0.02% |
| White vaseline | 10% |
| Liquid vaseline | q.s. |

TABLE 7

Illustrative Naltrexone Gel Formulation

| Ingredient | Amount (% by weight of the composition) |
| --- | --- |
| Naltrexone | 1% |
| Carbomer | 2% |
| Sodium hydroxide | 1.25% |
| Water | q.s |

We claim:

1. A method for treating a vesicular eruption caused by the varicella-zoster virus, the method comprising topically administering to a subject in need thereof an effective amount of naltrexone or a pharmaceutically-acceptable salt thereof, wherein the naltrexone or the pharmaceutically-acceptable salt thereof is administered in the form of a pharmaceutical composition comprising:
   a) the naltrexone or the pharmaceutically-acceptable salt thereof in an amount of about 0.1% to about 5% by weight of the pharmaceutical composition;
   b) an emulsifying agent in an amount of about 2% to about 5% by weight of the pharmaceutical composition;
   c) a stiffening agent in an amount of about 1% to about 45% by weight of the pharmaceutical composition;
   d) a surfactant in an amount of about 0.5% to about 2.5% by weight of the pharmaceutical composition;
   e) a preservative in an amount of about 0.01% to about 0.6% by weight of the pharmaceutical composition;
   f) a humectant in an amount of about 1% to about 15% by weight of the pharmaceutical composition;
   g) alkalizing or buffering agent in an amount of about 0.01% to about 3% by weight of the pharmaceutical composition;
   h) an emollient in an amount of about 1% to about 50% by weight of the pharmaceutical composition; and
   i) a solvent,
   wherein the vesicular eruption regresses within 5 days of administration of the pharmaceutical composition.

2. The method of claim 1, wherein the naltrexone or the pharmaceutically-acceptable salt thereof has less than about 10% by weight of other stereoisomers.

3. The method of claim 1, wherein the naltrexone or the pharmaceutically-acceptable salt thereof has less than about 5% by weight of other stereoisomers.

4. The method of claim 1, wherein the naltrexone or the pharmaceutically-acceptable salt thereof is present in an amount of about 0.5% to about 2% by weight of the pharmaceutical composition.

5. The method of claim 1, wherein the naltrexone or the pharmaceutically-acceptable salt thereof is present in an amount of about 1% by weight of the pharmaceutical composition.

6. The method of claim 1, wherein the pharmaceutical composition is in the form of a gel, cream, ointment, liquid, suspension, solution, emulsion, foam, or aerosol.

7. The method of claim 1, wherein the pharmaceutical composition is administered to the subject by spreading or spraying the composition onto the affected area.

8. The method of claim 1, wherein the naltrexone or the pharmaceutically-acceptable salt thereof is administered in a total daily dose of up to about 150 mg/cm$^2$ of skin.

9. The method of claim 1, wherein the naltrexone or the pharmaceutically-acceptable salt thereof is administered in a total daily dose of about 10 mg/cm$^2$ to about 100 mg/cm$^2$ of skin.

10. The method of claim 1, wherein the naltrexone or the pharmaceutically-acceptable salt thereof is administered in a total daily dose of about 50 mg/cm$^2$ of skin.

11. The method of claim 1, wherein the pharmaceutical composition is administered 1, 2, 3, 4, or 5 times daily.

12. The method of claim 1, further comprising administering to the subject one or more additional agents effective to treat the vesicular eruption.

13. The method of claim 12, wherein the additional agent is acyclovir, valacyclovir, or famciclovir.

14. The method of claim 1, wherein the administration blocks an opioid receptor in the subject.

15. The method of claim 14, wherein the opioid receptor that is blocked is a mu (μ) opioid receptor.

16. The method of claim 14, wherein the opioid receptor that is blocked is a delta (δ) opioid receptor.

17. The method of claim 14, wherein the opioid receptor that is blocked is a kappa (κ) opioid receptor.

18. The method of claim 1, wherein the method further comprises treating post-herpetic neuralgia caused by varicella-zoster virus in the subject.

19. The method of claim 1, wherein a pain of the subject associated with the varicella-zoster virus regresses within 3 days of administration.

20. The method of claim 1, wherein an itching of the subject associated with the varicella-zoster virus regresses within 3 days of administration.

21. The method of claim 1, wherein a hyperesthesis of the subject associated with the varicella-zoster virus regresses within 3 days of administration.

22. The method of claim 1, wherein an itching, pain, and hyperesthesis of the subject associated with the varicella-zoster virus regresses within 3 days of administration.

23. The method of claim 1, wherein no additional treatment is required to treat the vesicular eruption.

24. The method of claim 1, wherein the administration produces no side-effect in the subject.

25. The method of claim 1, wherein the administration occurs daily.

26. The method of claim 1, wherein the administration occurs three times daily.

27. The method of claim 1, wherein the naltrexone or the pharmaceutically-acceptable salt thereof is administered in a total daily amount of about 1 g.

28. The method of claim 1, wherein the pharmaceutical composition comprises:
    a) the naltrexone or the pharmaceutically-acceptable salt thereof in an amount of about 0.5% to about 2% by weight of the pharmaceutical composition;
    b) the emulsifying agent in an amount of about 2% to about 5% by weight of the pharmaceutical composition;
    c) the stiffening agent in an amount of about 2% to about 5% by weight of the pharmaceutical composition;
    d) the surfactant in an amount of about 0.5% to about 1.5% by weight of the pharmaceutical composition;
    e) the preservative in an amount of about 0.01% to about 0.6% by weight of the pharmaceutical composition;
    f) the humectant in an amount of about 2% to about 10% by weight of the pharmaceutical composition;
    g) the alkalizing or buffering agent in an amount of about 0.01% to about 3% by weight of the pharmaceutical composition;
    h) the emollient in an amount of about 15% to about 30% by weight of the pharmaceutical composition; and
    i) the solvent.

29. The method of claim 1, wherein the pharmaceutical composition comprises:
    a) the naltrexone or the pharmaceutically-acceptable salt thereof in an amount of about 1% by weight of the pharmaceutical composition;
    b) the emulsifying agent, wherein the emulsifying agent is cetyl alcohol in an amount of about 3.6% by weight of the pharmaceutical composition, and carboxypolymethylene in an amount of about 0.2% by weight of the pharmaceutical composition;
    c) the stiffening agent in an amount of about 3.6% by weight of the pharmaceutical composition, wherein the stiffening agent is stearyl alcohol;
    d) the surfactant in an amount of about 0.8% by weight of the pharmaceutical composition, wherein the surfactant is sodium lauryl sulfate;
    e) the preservative, wherein the preservative is nipagin in an amount of about 0.1% by weight of the pharmaceutical composition, and nipasol in an amount of about 0.05% by weight of the pharmaceutical composition;
    f) the humectant in an amount of about 5% by weight of the pharmaceutical composition, wherein the humectant is propylene glycol;
    g) the alkalizing or buffering agent in an amount of about 0.03% by weight of the pharmaceutical composition, wherein the alkalizing or buffering agent is sodium hydroxide;
    h) the emollient, wherein the emollient is white vaseline in an amount of about 13.5% by weight of the pharmaceutical composition, and liquid vaseline in an amount of about 5.4% by weight of the pharmaceutical composition; and
    i) the solvent, wherein the solvent is water.

* * * * *